United States Patent
Cavazza

(10) Patent No.: US 6,335,038 B1
(45) Date of Patent: Jan. 1, 2002

(54) COMPOSITION FOR THE PREVENTION AND/OR TREATMENT OF OSTEOPOROSIS AND ALTERATIONS DUE TO MENOPAUSE SYNDROME

(75) Inventor: Claudio Cavazza, Rome (IT)

(73) Assignee: Sigma-Tau Healthscience S.p.A., Pomezia (IT)

( * ) Notice: Subject to any disclaimer, the term of this patent is extended or adjusted under 35 U.S.C. 154(b) by 0 days.

(21) Appl. No.: 09/720,237

(22) PCT Filed: Jun. 17, 1999

(86) PCT No.: PCT/IT99/00174

§ 371 Date: Dec. 22, 2000

§ 102(e) Date: Dec. 22, 2000

(87) PCT Pub. No.: WO99/66913

PCT Pub. Date: Dec. 29, 1999

(30) Foreign Application Priority Data

Jun. 23, 1998 (IT) ........................................ RM98A0417

(51) Int. Cl.⁷ .............................................. A61K 35/78

(52) U.S. Cl. ........................ 424/757; 424/768; 424/436

(58) Field of Search ................................. 424/757, 768, 424/436

(56) References Cited

U.S. PATENT DOCUMENTS 5,702,752 A * 12/1997 Gugger et al.

FOREIGN PATENT DOCUMENTS

EP       0 773 020 A2 *  5/1997

* cited by examiner

Primary Examiner—Francisco Prats
Assistant Examiner—Susan D. Coe
(74) Attorney, Agent, or Firm—Oblon, Spivak, McClelland, Maier & Neustadt, P.C.

(57) ABSTRACT

A composition that may take the form of a dietary supplement or of a medicament is disclosed which comprises as active ingredients propionyl L-carnitine and the isoflavone genistein for the therapeutic treatment of osteoporosis and menopause syndrome.

18 Claims, No Drawings

COMPOSITION FOR THE PREVENTION AND/OR TREATMENT OF OSTEOPOROSIS AND ALTERATIONS DUE TO MENOPAUSE SYNDROME

The present invention relates to a composition for the prevention and/or treatment of osteoporosis and alterations due to menopause syndrome.

Accordingly the composition may take the form and exert the action of a dietary supplement or of an actual medicine, depending upon the support or preventive action, or the strictly therapeutic action, which the composition is intended to exert in relation to the particular individuals it is to be used in.

Particularly the present invention relates to a composition which comprises in combination:

(a) propionyl L-carnitine or a pharmacologically acceptable salt thereof, optionally in combination with at least another "carnitine" where for "carnitine" is intended L-carnitine or an alkanoyl L-carnitine selected from the group comprising acetyl-L-carnitine, valeryl L-carnitine, isovaleryl L-carnitine or their pharmacologically acceptable salts; and (b) 4',5,7-trihydroxyisoflavone (genistein) optionally in combination with at least another isoflavone selected from the group comprising 4',7-dihidroxyisoflavone (daidzein), its 7-glucoside (daidzin) and its 4,7-diglucoside.

The new composition can be orally, parenterally, rectally or transdermally administered and results particularly useful both to humans and animals, as a dietary supplement or as an actual medicine.

As is well known, postmenopausal syndrome is characterised by numerous manifestations including vascular effects ranging from hot flushes to an increased risk of cardiovascular accidents, as well as mental and mood disorders, and the occurrence of osteoporosis.

The risk of tumours also increases in this period.

Osteoporosis is a prevalent disease in elderly subjects, but it is particularly postmenopausal women who are most affected.

Osteoporosis, cardiovascular accidents and tumour risk are, in fact, the most frequent events in postmenopausal women.

The therapeutic approaches for the prevention and treatment of the pathological abnormalities accompanying this period are multiple and involve the use of minerals such as calcium, vitamins such as vitamin D, or calcitonin, but the most wide-spread therapy consists in hormone replacement treatment (HRT).

Oestrogen treatment, in fact, is clearly indicated in postmenopausal disorders as replacement therapy for a well documented deficiency of such hormones.

The use of these hormones, however, is by no means risk-free. Well known are the thromboembolic risks related to the use of oestrogens and these constitute one of the factors limiting their use. The most serious factor, however, is above all the carcinogenic risk. Oestradiol and progesterone, as well as dihydrotestosterone receptors have, in fact, been described in primary tumours of the large bowel and breast. Activation of these receptors has been postulated as one of the pathogenetic causes of these tumours.

Hormone replacement therapy (HRT) is associated with a series of side effects consisting not only in the thromboembolic and carcinogenic risk, but also in weight gain, headache, nausea, depression, and breast swelling and tension.

Additional manifestations regarded as contraindications are the presence of endometriosis, uterine fibroids or previous breast and uterine tumours, which often prompt the physician to abandon this type of therapy and look for other safer solutions.

Isoflavones and phyto-oestrogens would appear to offer a valid alternative.

The indication that vegetable derivatives are capable of exerting an oestrogen-like action has emerged from the finding that animals fed on Medicago sativa or Trifolium repens present disorders of the reproductive capability. The cause of this effect has been traced to the presence in these plants of coumesterol, a substance structurally similar to oestradiol and classed among the phyto-oestrogens.

Substances which are naturally occurring in the vegetable world with structures and functions similar to 17β-oestradiol are regarded as phyto-oestrogens. This category includes numerous compounds such as lignans, isoflavones, coumestans and lactones of resorcylic acid. Phyto-oestrogens are present in many cereals and legumes. Legumes such as soy are particularly rich in isoflavones, while lignans are present in almost all cereals and, above all, in linseed oil.

Phyto-oestrogens may derive from precursors present in the diet after bacterial modification in the stomach or gut.

The main derivatives from bacterial modification of lignans are. enterodiol and enterolactone, whereas the main isoflavone derivatives after bacterial removal of the glycoside part are genistein, daidzein and equol.

Most of these phyto-oestrogens have been identified in human plasma and saliva, as well as in prostate fluid and mammary cyst aspirate.

All phyto-oestrogens possess oestrogen-like activity, though it is inferior to that of oestradiol.

Epidemiological research has demonstrated a lower incidence of breast, ovarian and large bowel tumours in populations consuming diets containing substantial amounts of isoflavones than in those consuming only small amounts of these substances.

There is a marked difference in this sense between Asiatic and Western populations.

The prognosis, e.g. of breast tumours, is also better in Asiatic populations such as the Japanese than in those of the U.S. or Great Britain.

In-vitro studies, moreover, have confirmed the antiproliferative activity of phyto-oestrogens, as assessed in breast tumour cell lines.

In the case of osteoporosis, too, it has been found that the incidence of this disease increases in relation to an oestrogen deficiency and is lower in Asiatic populations with a diet rich in isoflavonoids than in Western populations.

It has recently been postulated that phyto-oestrogens may behave differently, at oestrogen receptor level, according to the different tissues, as is the case with the synthetic oestrogens such as tamoxifen or 4-hydroxytamoxifen which act as antagonists at the level of the oestrogen receptors of breast tissue and as partial agonists at the level of the vessels and bone tissue.

As regards genistein (4',5,7-trihydroxyisoflavone), we should also consider other mechanisms of action such as inhibition of membrane ATPase and inhibition of tyrosine kinase and topoisomerase II.

It has also been reported that genistein exerts a direct metabolic effect on bone metabolism and that it is capable of inhibiting bone reuptake in in-vitro cultures of femoral metaphyseal tissue. Genistein also protects the endothelial cells against atherogenic risk and prevents or inhibits tumour development. The tumour risk, however, generally appears to be reduced not only by intake of genistein but also by soy extracts.

Among the various isoflavones, genistein and daidzin appear to be the ones that show the closest interaction with oestrogen receptors.

These properties make phyto-oestrogens valid candidates as substitutes for oestradiol, presenting none of the latter's side effects and proving suitable for practically unlimited ingestion, as occurs in those populations whose diets include substantial consumption of vegetables and legumes.

The metabolic actions of the carnitines are very well known. L-carnitine, acetyl L-carnitine, propionyl L-carnitine and isovaleryl L-carnitine all present practically the same activity at the mitochondrial level and at the level of β-oxidation of fatty acids, though with some differences according to their kinetics and the tissues considered.

The carnitines also exert a substantial antioxidant action, thereby providing a protective effect against lipoperoxidation of the phospholipid membrane and against oxidative stress induced at myocardial and endothelial cell level.

The carnitines have also proved to be active on carbohydrate metabolism. In the course of ageing, tissue carnitine concentrations diminish and therefore so do the metabolic possibilities of the various tissues. Particularly adversely affected are tissues such as bone tissue which require a continuous reconstructive and metabolic functional capability on the part of the osteoblasts for maintenance of bone mass.

Surprisingly, it has now been found that a combination composition comprising as characterising ingredients:

(a) propionyl L-carnitine or one of its pharmacologically acceptable salts; and
(b) 4',5,7-trihydroxyisoflavone (genistein)

is extremely effective in the prevention and/or therapeutic treatment of osteoporosis and postmenopause syndrome as a result of the potent synergistic action exerted by its ingredients.

It has also been found that, advantageously, ingredient (a) may further comprise a "carnitine" selected from the group consisting of L-carnitine, acetyl L-carnitine, valeryl L-carnitine, isovaleryl L-carnitine or their pharmacologically acceptable salts or mixtures and that ingredient (b) may further comprise an isoflavone selected from the group consisting of 4',7-dihyrdoxyisoflavone (daidzein), its 7-glycoside (daidzin) and its 4,7-diglycoside or mixture of thereof.

The (a):(b) weight-to-weight ratio ranges from 0.01 to 1:1. In the composition, ingredient (b) can be present in the form of an extract of vegetable products containing it, such as, for example, soybean seeds or linseed.

Described here below are a number of tests demonstrating the low toxicity and good tolerability of the composition according to the invention as well as the intense synergistic effect produced by its ingredients.

Toxicological Tests

Both the single-dose and prolonged administration of a carnitine mixture (combination consisting of L-carnitine+ acetyl L-carnitine+propionyl L-carnitine+isovaleryl L-carnitine with a weight-to weight ratio of 1:1 between the various carnitines), or propionyl L-carnitine, or the mixture of soy isoflavones, or genistein, given for the purposes of evaluating both the acute and chronic toxicity of the combinations according to the invention, demonstrated the low toxicity and good tolerability of the products, whether administered alone or in combination.

With the single-dose regimen, it proved possible to administer, both to rats and mice, a dose of 600 mg/kg of carnitine mixture, or 600 mg/kg of propionyl L-carnitine alone, or 5 g/kg of a soy extract containing 5% isoflavones, or 15 mg/kg of genistein, or various combinations of these products, without any mortality or evident signs of toxicity occurring in the animals thus treated. Equally well tolerated was the prolonged administration to rats for thirty days consecutively of 2 g/kg of a soy extract containing 5% isoflavones together with 200 mg/kg of carnitine mixture or with 150 mg/kg of propionyl L-carnitine, as well as 5 mg/kg genistein administered in combination for the same period either with the carnitine mixture or with propionyl L-carnitine. In these tests, too, at the end of the thirtieth day of treatment, no abnormalities of a toxic nature were found either in the various blood-chemistry tests performed or in the red and white blood cell counts. The histological examination performed on the main organs also failed to reveal any significant abnormalities.

Evaluation of Chances in Osteocalcin Concentration

There is a close correlation between changes in plasma levels of osteocalcin and bone tissue osteoblast activity, and a reduction in osteocalcin plasma levels is an indicator of increased osteoblast activity which appears to underlie osteoporosis in elderly subjects or in the postmenopausal period in women. These tests were performed on a batch of mice aged at least 7 months, divided into various groups of 10 mice each.

While one group was used as a control group, the other groups were administered, with their diet, the carnitine mixture (100 mg/kg) consisting, in these tests, as in the others, of a mixture of L-carnitine+acetyl L-carnitine+ propionyl L-carnitine+isovaleryl L-carnitine in a weight-to-weight ratio of 1:1, or propionyl L-carnitine (100 mg/kg), or soy extract containing 5% isoflavone (2 g/kg), or genistein (5 mg/kg), or various combinations of these ingredients. The treatment was administered daily for thirty days or sixty days consecutively. The serum osteocalcin assay was performed according to the method described by Grunhaberg (Grunhaberg et al., *Meth. Enzymology*, 207, 516, 1984) taking blood samples from control and treated animals from the supraorbital region.

As can be seen from the results presented in Table 1, the administration of the carnitine mixture, or propionyl L-carnitine, or soy extract, or genistein was capable of increasing the serum osteocalcin concentrations of the animals thus treated, whereas serum osteocalcin levels tended to decrease with age in the control animals. Surprisingly, however, the highest increases were observed after combined administration of the carnitine mixture plus soy extract, as well as after administration of the combination of propionyl L-carnitine plus genistein.

The increases in osteocalcin concentrations were even more marked in the mice treated for sixty days consecutively, while the control animals treated for sixty days showed an even more marked age-related reduction in osteocalcin levels.

The results of these tests demonstrate, therefore, that there is a clearly detectable potent synergistic effect between the carnitines considered and the isoflavones, and particularly between propionyl L-carnitine and genistein. The synergistic effect of the combination appears to be unpredictable and unsuspected in view of the effects obtainable with the single isolated ingredients of the combination according to the invention.

Prostacyclin Synthesis Tests

Prostacyclin ($PGI_2$) is one of the products formed by the action of cyclo-oxygenase at the level of a fatty acid such as arachidonic acid and, unlike $(PG)E_2$ or leukotrienes such as $(LT)C_1$, it does not possess the inflammatory, vasculospastic, osteoclastic or thrombotic-type activities of the prostaglandins, but rather a very appreciable cytoprotective, vasodilator and osteoblastic activity, and its formation is related to the activity of $COX_1$ rather than to that of $COX_2$.

The purpose of these tests was to establish whether the administration to rats of the carnitine mixture (L-carnitine+acetyl L-carnitine+propionyl L-carnitine+isovaleryl L-carnitine in a weight-to-weight ratio of 1:1 to one another), or soy extract, or genistein, or propionyl L-carnitine, or various combinations of these products might lead to an increase in the production of prostacyclin (PGI2). It has been demonstrated, in fact, that the prostaglandins, and prostacyclin in particular, may regulate the production of insulin-like growth factor (IGF-1) and thereby influence chondrocyte metabolism.

As is known, moreover, there is a close correlation between IGF-1 and growth hormone, and it has been proved that the latter, amongst its other positive effects on growth, is capable of playing an important role in bone remodelling and in osteoblast activity. Prostaglandins can also regulate several other hormone effects, including those of oestrogens.

The method used in these tests was the one described by G. R. Elliot in *Brit. J. Nutrition,* 64, 497, 1990, measuring the release of prostaglandins by peritoneal macrophages isolated from a batch of rats that were administered either the carnitine mixture, or the soy extract, or propionyl L-carnitine, or genistein, or various combinations of these products with their diet for seven days consecutively. The doses given were 400 mg/kg of carnitine mixture, or 400 mg/kg of propionyl L-carnitine, or 8 g/kg of soy extract, or 40 mg/kg of genistein, or the same doses of the various products combined. On day 1 of treatment, all the animals were treated intraperitoneally with 2 $cm^3$ of solution containing 2 mg of carrageenin. After the last day of treatment, peritoneal macrophages were isolated from the controls and treated rats so as to obtain a $2 \times 10^{-6}/cm^3$ cell suspension.

One $cm^3$ of the macrophage preparation thus prepared was incubated for a period of two hours in order to evaluate the basal release or release after 30 minutes after being placed in contact with an ionophore such as A2318. The cells were centrifuged and the supernatant analysed for its $PGI_2$ content according to the radioimmunological assay method described by Zijstra et al. (Zijstra, F. J., Vincent, J. E., *J. Chromatography,* 311, 39, 1984).

As can be seen from the results reported in Table 2, administration of the carnitine mixture and of propionyl L-carnitine leads to an increase in $PGI_2$ synthesis in macrophages from the rats treated, whereas the increase appears only modest in rats treated with soy extract or with genistein. The increase in $PGI_2$ synthesis, however, appears to be of major proportions in rats treated with a combination of carnitines plus soy extract, or with a combination of propionyl L-carnitine plus soy extract or genistein.

The increase in prostacyclin release by macrophages from animals treated with these combinations shows a marked potent synergistic effect.

Osteoblastic Cell Growth Tests

In view of the important role played by osteoblasts in regulating growth and in bone remodelling, a series of tests was conducted to evaluate whether the presence of carnitines or isoflavonoids and genistein could influence the growth of osteoblastic cells in vitro. To this end, mouse osteoblastic cells (MC3T3 osteoblast-like cells), after being trypsinated and placed in a medium enriched with heat-inactivated 2% foetal calf serum, were grown on plates (with wells each containing ca. 10,000 cells) in the presence or absence of carnitine mixture (combination of L-carnitine+acetyl L-carnitine+propionyl L-carnitine+isovaleryl L-carnitine in a weight-to weight ratio of 1:1), or propionyl L-carnitine, or isoflavones, or genistein, which were added to the culture medium after suitable solubilisation at concentrations ranging from 0.05 mM of carnitine to 0.005 mM of isoflavones or genistein. After a 72-hour incubation, the number of cells was counted with a colorimetric method via reduction of dimethylthiazole-diphenyltetrazole according to the technique described by Riancho (Riancho, J. A., *J. Bone Mineer. Res.,* 10, 439, 1995). The results are shown in Table 3.

As can be seen from the results obtained in these tests, whereas the carnitine mixture and propionyl L-carnitine have a modest effect on the growth of cells incubated with them, neither the isoflavones nor genistein appear to influence the normal growth rate of the cells as compared with controls.

The combination of isoflavones or genistein with the carnitine mixture or with propionyl L-carnitine significantly speeds up the growth of osteoblasts and does so to a much greater extent than is achieved with the use of carnitines alone.

In these tests, too, then, a substantial, unexpected synergistic effect between carnitines and soy extract or genistein is achieved.

TABLE 1

Serum concentrations of osteocalcin in mice treated with 100 mg/kg of carnitine mixture (L-carnitine 25 mg + acetyl L-carnitine 25 mg + propionyl L-carnitine 25 mg + isovaleryl L-carnitine 25 mg), or with 100 mg/kg of propionyl L-carnitine, or with 100 mg/kg of soy extract containing 5% isoflavones, or with 100 mg/kg of genistein, or with various combinations of these products.

| | Osteocalcin (ng/ml) Duration of treatment | |
|---|---|---|
| Treatment | 30 days | 60 days |
| Controls | 120.4 ± 8.6 | 90.5 ± 7.9 |
| Carnitine mixture | 136.2 ± 9.5 | 109.4 ± 8.7 |
| Propionyl L-carnitine | 130.7 ± 10.1 | 98.5 ± 8.1 |
| Soy extract | 139.4 ± 11.6 | 112.7 ± 9.4 |
| Genistein | 135.9 ± 10.2 | 100.1 ± 10.2 |
| Carnitine mixture + soy extract | 295.6 ± 19.8 | 250.5 ± 20.3 |
| Carnitine mixture + genistein | 285 ± 20.1 | 245.9 ± 19.8 |
| Propionyl L-carnitine + genistein | 289 ± 20.9 | 258.1 ± 20.6 |

TABLE 2

Evaluation of the effect of administration of carnitine mixture, propionyl L-carnitine, soy extract or genistein, or various combinations of these, on prostacyclin synthesis in rat peritoneal macrophages.

| Treatment | Macrophage $PGI_2$ release values compared with controls (ng/2 × $10^{-6}$ cells) |
|---|---|
| Controls | 0.25 ± 0.03 |
| Carnitine mixture | 2.7 ± 0.15 |
| Propionyl L-carnitine | 3.0 ± 0.22 |

TABLE 2-continued

Evaluation of the effect of administration of carnitine mixture, propionyl L-carnitine, soy extract or genistein, or various combinations of these, on prostacyclin synthesis in rat peritoneal macrophages.

| Treatment | Macrophage PGI$_2$ release values compared with controls (ng/2 × 10$^{-6}$ cells) |
|---|---|
| Soy extract | 0.35 ± 0.15 |
| Genistein | 0.39 ± 0.27 |
| Carnitine mixture + soy extract | 4.7 ± 0.31 |
| Carnitine mixture + genistein | 4.8 ± 0.51 |
| Propionyl L-carnitine + soy extract | 7.2 ± 0.45 |
| Propionyl L-carnitine + genistein | 6.6 ± 0.55 |

TABLE 3

Effect of carnitine mixture, propionyl L-carnitine, soy extract or genistein, alone and in various combinations, on MC3T3 osteoblast-like cells.

| Treatment | Percentage growth values compared with controls |
|---|---|
| Carnitine mixture | +15 ± 0.9 |
| Propionyl L-carnitine | +18 ± 1.2 |
| Soy extract | −8 ± 0.5 |
| Genistein | +5 ± 1.5 |
| Carnitine mixture + soy extract | +26 ± 2.5 |
| Carnitine mixture + genistein | +28 ± 3.3 |
| Propionyl L-carnitine + soy extract | +25 ± 6.0 |
| Propionyl L-carnitine + genistein | +31 ± 4.0 |

Some illustrative, non-limiting examples of formulations according to the invention, are reported hereinbelow:

| | |
|---|---|
| 1) Carnitine mixture | mg 500 |
| (L-carnitine mg 125, acetyl L-carnitine mg 125, propionyl L-carnitine mg 125, isovaleryl L-carnitine mg 125) | |
| Soy extract (titled 5% in isoflavon) | mg 500 |
| 2) Carnitine mixture | mg 200 |
| (L-carnitine mg 50, acetyl L-carnitine mg 50, propionyl L-carnitine mg 50, isovaleryl L-carnitine mg 50) | |
| Soy extract (titled 5% in isoflavon) | mg 200 |
| 3) Propionyl L-carnitine | mg 500 |
| Soy extract (titled 5% in isoflavon) | mg 500 |
| 4) Propionyl L-carnitine | mg 200 |
| Soy extract (titled 5% in isoflavon) | mg 200 |
| 5) Carnitine mixture | mg 500 |
| (L-carnitine mg 125, acetyl L-carnitine mg 125, propionyl L-carnitine mg 125, isovaleryl L-carnitine mg 125) | |
| Genistein | mg 25 |
| 6) Carnitine mixture | mg 200 |
| (L-carnitine mg 50, acetyl L-carnitine mg 50, propionyl L-carnitine mg 50, isovaleryl L-carnitine mg 50) | |
| Genistein | mg 10 |
| 7) Propionyl L-carnitine | mg 500 |
| Genistein | mg 10 |
| 8) Propionyl L-carnitine | mg 200 |
| Genistein | mg 10 |
| 9) Carnitine mixture | mg 200 |
| (L-carnitine mg 50, acetyl L-carnitine mg 50, propionyl L-carnitine mg 50, isovaleryl L-carnitine mg 50) | |
| Soybean seeds extract (titled 5% in isoflavon) | mg 200 |
| Isoflavonic extract of linseeds | mg 50 |
| Vit. D | mg 5 |
| Calcium | mg 50 |
| Vit. E. | mg 20 |
| CoQ10 | mg 10 |
| Chromium | mg 5 |
| Zinc | mg 5 |
| Magnesium | mg 5 |
| Selenium methionine | mg 0.1 |
| Pyridoxine | mg 20 |
| Vit. C | mg 50 |
| 10) Carnitine mixture | mg 250 |
| L-carnitine mg 75, acetyl L-carnitine mg 75, propionyl L-carnitine mg 75, isovaleryl L-carnitine mg 75) | |
| Soybean seeds extract (titled 5% in isoflavon) | mg 250 |
| Eicosapentaenoic Acid (EPA) | mg 50 |
| Docosahexaenoic Acid (DHA) | mg 25 |
| Isoflavonic extract of linseeds | mg 50 |
| Resveratrol | mg 2 |
| Vit. D | mg 5 |
| Calcium | mg 50 |
| Vit. E. | mg 10 |
| CoQI0 | mg 10 |
| Chromium | mg 5 |
| Zinc | mg 5 |
| Magnesium | mg 5 |
| Selenium methionine | mg 0.1 |
| Pyridoxine | mg 50 |
| Vit. C | mg 50 |

What is meant by pharmacologically acceptable salt of L-carnitine or alkanoyl L-carnitine is any salt of these active ingredients with an acid that does not give rise to unwanted toxic or side effects. These acids are well known to pharmacologists and pharmacy experts.

Non-limiting examples of suitable salts are the following: chloride; bromide; iodide; aspartate, acid aspartate; citrate, acid citrate; tartrate; phosphate, acid phosphate; fumarate; acid fumarate; glycerophosphate; glucose phosphate; lactate; maleate, acid maleate; orotate; oxalate, acid oxalate; sulphate, acid sulphate, trichloroacetate, trifluoroacetate and methanesulphonate.

A list of FDA-approved pharmacologically acceptable salts is given in *Int. J. of Pharm.* 33, (1986), 201–217; this latter publication is incorporated herein by reference.

The composition of the present invention can also comprise vitamins, coenzymes, mineral substances and antioxidants.

Suitable excipients to be used for formulating the compositions, having regard to the administrattion route of choice, shall be apparent to pharmacy and food industry experts.

What is claimed is:

1. A composition, which comprises:
   a) propionyl L-carnitine or a pharmacologically acceptable salt thereof; and
   b) 4',5,7-trihydroxyisoflavone, each being present in an amount effective for the treatment of osteoporosis or menopause syndrome or both.

2. The composition of claim 1, wherein ingredient a) further comprises a carnitine comprising L-carnitine, valeryl L-carnitine, isovaleryl L-carnitine or the pharmacologically acceptable salts thereof or mixtures thereof.

3. The composition of claim 1, wherein ingredient b) further comprises an isoflavone comprising 4',7-dihydroxyisoflavone (daidzein), the 7-glucoside thereof (daidzin), the 4,7-diglucoside thereof or mixtures thereof.

4. The composition of claim 1, wherein the ratio of a):b) is from 1:0.01 to 1:1.

5. The composition of claim 1, wherein the ingredient b) is in the form of vegetal extracts which comprise said ingredient b).

6. The composition of claim 5, wherein said vegetal extracts comprise soybean seed or linseed extracts.

7. The composition of claim 1, wherein the pharmacologically acceptable salt of L-carnitine or alkanoyl L-carnitine is selected from the group consisting of chloride, bromide, iodide, aspartate, acid aspartate, citrate, acid citrate, tartrate, phosphate, acid phosphate, fumarate, acid fumarate, glycerophosphate; glucose phosphate, lactate, maleate, acid maleate, orotate, acid oxalate, sulphate, acid sulphate, trichloroacetate, trifluoroacetate and methane sulfonate.

8. The composition of claim 1, which further comprises vitamins, coenzymes, mineral substances or antioxidants or a combination thereof.

9. The composition of claim 1, which is in a form of an orally administrable dietary supplement.

10. The composition of claim 6, wherein said vegetal extracts comprise soy extract.

11. The composition of claim 8, wherein said vitamins comprise vitamins C, D or E or a mixture thereof.

12. The composition of claim 8, wherein said mineral substances comprise substances containing calcium, chromium, magnesium, or selenium or a mixture thereof.

13. The composition of claim 1, which is in the form of an orally, parenterally, rectally or transdermally administrable medicament.

14. The composition of claim 13, which is in a form of pills, tablets, capsules, granulates, syrup, vials or drops.

15. The dietary supplement of claim 14, which is in a solid form.

16. The dietary supplement of claim 14, which is in a semi-solid or liquid form.

17. The dietary supplement of claim 14, which is in a form of pills, tablets, capsules, granulates or syrup.

18. A dietary supplement, comprising:
a) the composition of claim 1, and
b) a carrier.

* * * * *

UNITED STATES PATENT AND TRADEMARK OFFICE
CERTIFICATE OF CORRECTION

PATENT NO.   : 6,335,038 B1
DATED        : January 1, 2002
INVENTOR(S)  : Claudio Cavazza It is certified that error appears in the above-identified patent and that said Letters Patent is hereby corrected as shown below:

Column 10,
Lines 9-17, please replace claims 15, 16, 17 and 18 with the following:
-- 15.   A dietary supplement, comprising:
    a) the compostion of claim 1, and
    b) a carrier.
16. The dietary supplement of claim 15, which is in a solid form.
17. The dietary supplement of claim 15, which is a semi-solid or liquid form.
18. The dietary supplement of claim 15, which is a form of pills, tablets, capsules, granulates or syrup. --

Signed and Sealed this

Twenty-fifth Day of March, 2003

JAMES E. ROGAN
*Director of the United States Patent and Trademark Office*